United States Patent [19]

Yannas et al.

[11] 4,252,759
[45] Feb. 24, 1981

[54] CROSS FLOW FILTRATION MOLDING METHOD

[75] Inventors: Ioannis V. Yannas, Newton Center, Mass.; David L. Sieverding, Houston, Tex.

[73] Assignee: Massachusetts Institute of Technology, Cambridge, Mass.

[21] Appl. No.: 29,229

[22] Filed: Apr. 11, 1979

Related U.S. Application Data

[62] Division of Ser. No. 837,051, Sep. 28, 1977, abandoned.

[51] Int. Cl.³ .............................................. B28B 1/26
[52] U.S. Cl. ........................................ 264/86; 264/87; 425/84; 425/447
[58] Field of Search .................. 425/84, 85, 447; 264/86, 87

[56] References Cited

U.S. PATENT DOCUMENTS

| | | | |
|---|---|---|---|
| 2,528,643 | 11/1950 | Dubbs | 425/85 |
| 2,632,227 | 3/1953 | Steele et al. | 264/86 |
| 2,671,940 | 3/1954 | Billner | 425/85 |
| 2,803,043 | 8/1957 | Stephens | 264/86 |
| 2,964,822 | 12/1960 | Tomkins | 264/86 |
| 3,021,254 | 2/1962 | Helversen et al. | 425/84 |
| 3,205,128 | 9/1965 | Justus et al. | 425/85 |
| 3,259,677 | 7/1966 | Zwick | 264/86 |
| 3,280,237 | 10/1966 | Corbin et al. | 264/86 |
| 3,627,519 | 4/1969 | Baker | 264/86 |
| 3,819,785 | 6/1974 | Argyle et al. | 264/86 |
| 3,880,972 | 4/1975 | Towne et al. | 264/87 |
| 4,124,669 | 11/1978 | Urmston | 264/86 |

Primary Examiner—Donald J. Arnold
Attorney, Agent, or Firm—Arthur A. Smith, Jr.; David E. Brook

[57] ABSTRACT

A cross flow filtration molding apparatus and method are disclosed which are particularly useful for forming complicated shapes from dispersions of particles in a liquid medium. Dispersion is pumped through a mold which has porous walls and a sufficient pressure differential is applied to drive a portion of the liquid medium through the porous walls which results in deposition of particles on the walls to form a shaped article. The shaped article may inherently have sufficient structural integrity, or it may be post-treated to provide additional structural integrity.

5 Claims, 6 Drawing Figures

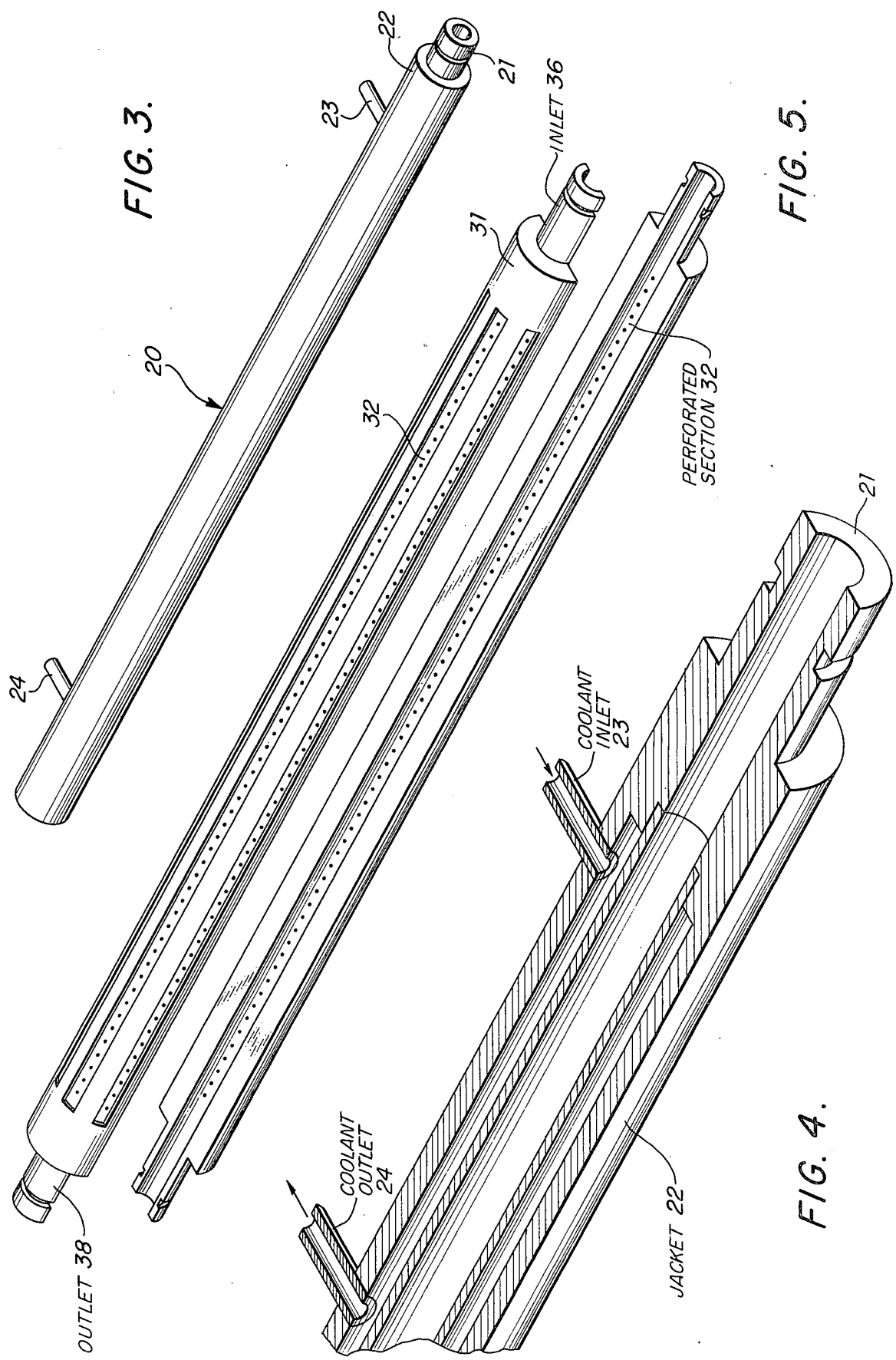

CROSS FLOW FILTRATION MOLDING METHOD

GOVERNMENT SPONSORSHIP

Work relating to this invention was partially supported by a contract from the National Institutes of Health, Contract No. NIH-N01-HB-4-2969.

This is a, division, of application Ser. No. 837,051, filed Sept. 28, 1977 and now abandoned.

BACKGROUND OF THE INVENTION

1. Field of the Invention

This invention is in the field of forming shaped articles from dispersions and has particular application to the molding of shaped articles from a suspension of solid particles in a liquid medium.

2. Description of the Prior Art

There are materials which are difficult to form into shaped articles by traditional molding processes. These processes typically utilize either heat or solvents, and these can cause deleterious changes in such materials. Examples include the loss of molecular structure which collagen undergoes when heated; the loss of molecular orientation or change in crystallinity or in shape which polyester fibers undergo during molding; th damage to glass fibers which would occur in a molding operation; the loss of fiber shape which would occur if polyacrylonitrile fibers were molded into a mat or nonwoven fabric by prior suspension in a relatively volatile solvent such as dimethyl formamide, etc.

In addition, some materials are infusible and insoluble, which means that the traditional molding processes are simply not applicable.

One well known process for forming articles from infusible, insoluble dispersions is that process used in paper making. In this process, a dispersion of particles of paper pulp is concentrated by a filtration process which occurs using gravity-induced deposition of particles to leave behind a highly concentrated, viscous, gel-like substance which can be subsequently dried to produce sheets of paper. This method, however, relies upon the force of terrestrial gravity, which is unidirectional and which cannot be controlled. Therefore, deposition of the concentrated gel-like substance can only take place on a planar surface, and the process is limited to forming sheets. More complicated shapes cannot be fabricated, except by first forming sheets and subsequently forming the sheets into the more complicated shapes. This invariably results in the presence of seams which cannot be tolerated in many applications, such as the formation of vascular protheses, etc., from biocompatible materials. Seams are also undesirable in the manufacture of containers, e.g., milk cartons, since an additional processing step is required to close them up, often by use of an adhesive or metal staples. Seams also usually constitute areas of inherent mechanical weakness where failure is more likely.

Recently, a new class of biocompatible materials comprising crosslinked reaction products of collagen and a mucopolysaccharide has been disclosed. See U.S. patent applications Ser. Nos. 596,111 abandoned and 596,112, filed July 15, 1976, now U.S. Pat. No. 4,060,081 in the names of Yannas et al. These are infusible, insoluble materials, which are particularly ueful for vascular prostheses, etc. Papermaking processes are unsatisfactory for forming vascular prostheses from these materials, because of the presence of seams which cause blood-clotting when these prostheses are implanted. Other methods for forming articles from collagen-based materials are also not satisfactory.

One widely used method of forming articles from dispersions of collagen involves extrusion, often into a non-solvent such as acetone, alcohol or a salt solution. Many times an extrusion method is used, for example, to form surgical sutures or edible sausage casings from collagen materials. See, for example, U.S. Pat. Nos. 3,123,482; 3,114,372; 3,114,593; and 1,548,504. While extrusion is suitable for certain simple shapes, such as straight tubes, sheets, films, fibers, sutures, etc., it does not lend itself to the fabrication of more complicated shapes such as tubes having one or more bifurcations.

Lyophilization is another shaping technique used to make highly porous articles such as surgical spones or absorbent mats from collagen based materials. See, for example, U.S. Pat. Nos. 3,632,371; 3,471,598; 3,368,911; and 2,610,625. Lyophilization does not offer the degree of control required to form complicated vascular prostheses, however.

Electrodeposition is still another method referred to in the literature which makes use of the fact that collagen molecules carry a net electric charge outside the range of their isoelectric pH and move towards an electrode which can be any desired shape such as a tube. This technique is described in U.S. Pat. No. 3,446,939 as well as in Schmitt, F. O., *J. Amer. Leather Chem. Assoc.* 46,538 (1951). This technique is not applicable to the forming of crosslinked collagen-mucopolysaccharide materials because complexation and crosslinking of collagen leads to partial or total neutralization of the positive charges carried by the collagen molecule. Additionally, it is also difficult to prepare electrodes having the complicated shapes required for various prostheses formed from the crosslinked collagen-mucopolysaccharide biocompatible materials.

SUMMARY OF THE INVENTION

This invention relates to a new molding apparatus and process for forming articles with a predetermined shape from dispersions of particles in a liquid medium. The process is referred to herein as a cross flow filtration molding process.

The molding apparatus includes a mold with porous walls having the predetermined shape. The porous walls contain pores having a size sufficient to retain dispersed particles on the wall surface as liquid medium passes through the walls.

Means for introducing dispersion to the mold are also present, and typically comprise a pump for pumping dispersion through the mold.

Means for applying hydrostatic pressure to dispersion in the porous mold are also part of the apparatus. Typically, such means for applying might be a source of compressed gas attached to a reservoir for the dispersion. The reservoir and a flow development module to eliminate hydrodynamic end effects in the mold are optionally employed.

The cross flow filtration molding process comprises pumping a dispersion of particles through a mold having porous walls which allow transport of a portion of the dispersion medium therethrough. Hydrostatic pressure is applied to drive dispersion medium through the porous mold walls thereby causing particles to deposit on the mold walls to form an article having the predetermined shape. After sufficient particles have deposited to provide the shaped article with the wall thicknesses desired, the flow of dispersion through the mold is halted. The shaped article can be treated, in situ, or removed and subsequently treated to provide it with significantly improved structural integrity. Structural integrity might be provided, for example, by crosslinking a shaped article formed from deposited particles of collagen-mucopolysaccharide. In another embodiment, a mat of polyacrylonitrile fibers deposited as described herein could be provided with increased structural integrity by treating the molded fibrous mat with a relatively volatile solvent such as dimethyl formamide. In this case, brief exposure of the fibers to the solvent introduces fiber-fiber contacts which solidify after solvent removal to firmly bind individual fibers to each other. Post-treatment of a molded fibrous mat, prepared by cross flow filtration molding of thermoplastic fibers, e.g., chopped strands of polyester fibers, by controlled application of heat, could also serve to bond the fibers together. In another embodiment, a porous mat of glass fiber monofilaments, formed by the process described here, could be stabilized into a fiber-reinforced composite material by impregnating the formed mat with a liquid thermosetting polymer formulation, such as an epoxy formulation.

The cross flow filtration molding apparatus and method described herein offer significant advantages in the molding of shaped mats, nonwoven fabrics or nonporous articles from many dispersions compared to previously known molding techniques. For example, this apparatus and method can make use of hydrostatic pressure rather than gravity to deposit particles in a predetermined shape. Use of hydrostatic pressure, an isotropic force field, rather than gravity, a uniaxial force field, insures that deposition of particles will occur on all sites of the porous mold wall irrespective of the location of a particular site relative to any other site on the mold wall or relative to any reference axis, such as the direction of gravity acceleration. The flexibility thereby gained can be used to fabricate articles of a great variety of shapes by depositing particles from a dispersion on the walls of a mold having a predetermined shape, the latter not being limited by any directionality in the force field which drives the deposition process. An isotropic force field also results in an even deposition of particles at all locations so that wall thicknesses of molded products are uniform. It is also clear that, since it is the pressure difference across the mold wall which causes particle deposition, other means of establishing the pressure difference could also be employed, such as the subjection of the mold exterior to vacuum.

Additionally, cross flow filtration molding can be used to form shaped articles from a wide variety of dispersions. The process is, in fact, suitable for dispersions having relatively small particles, such as the cross-linked collagen-mucopolysaccharide biocompatible materials previously mentioned, or relatively large particles such as polyacrylonitrile fibers or chopped polyester strands. It is not limited by the type of liquid medium emloyed in the dispersion.

Since the process does not depend upon the migration of ions towards an electrode, it can be used with dispersions of particles which carry little or no ionic charge either due to the intrinsic non-electrolytic character of the substances constituting the dispersion or due to any conditions, such as pH, which might reduce or abolish the net charge on particles that are constituted from one or more polyelectrolytes.

The process also offers an advantage over extrusion into a non-solvent since it is often difficult to find suitable non-solvents and since it is difficult to design and fabricate extrusion dies for complicated shapes.

BRIEF DESCRIPTION OF THE DRAWINGS

FIG. 3 is a perspective view illustrating a flow development module suitable for use in the cross flow filtration molding apparatus of FIG. 1;

FIG. 4 is a cutaway perspective view of the flow development module of FIG. 3;

FIG. 5 is a perspective view of a split porous mold for forming elongated tubes suitable for use in the cross flow filtration apparatus of FIG. 1; and, FIG. 6 is a cross-sectional view of the mold of FIG. 5 also illustrating the insertion of filter paper therein.

DESCRIPTION OF PREFERRED EMBODIMENTS

Preferred embodiments of the invention will now be described by referring to the above-mentioned Figures in more detail.

Figure 1:
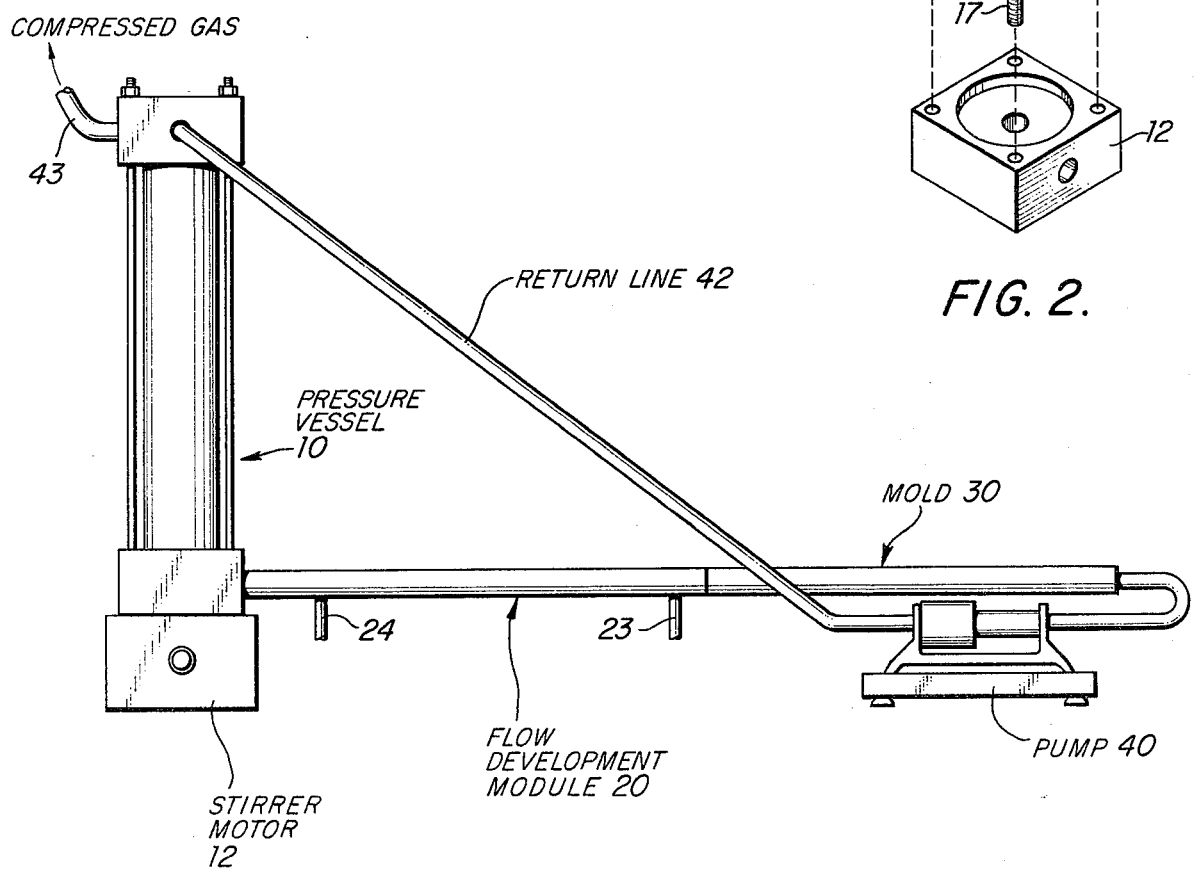
FIG. 1 is a schematic illustration of cross flow filtration molding apparatus according to this invention.

FIG. 1 illustrates a cross flow filtration molding apparatus formed from reservoir 10, flow development module 20, mold 30, pump 40 and dispersion return line 42. Each of these components in the overall molding apparatus will now be described.

Figure 2:
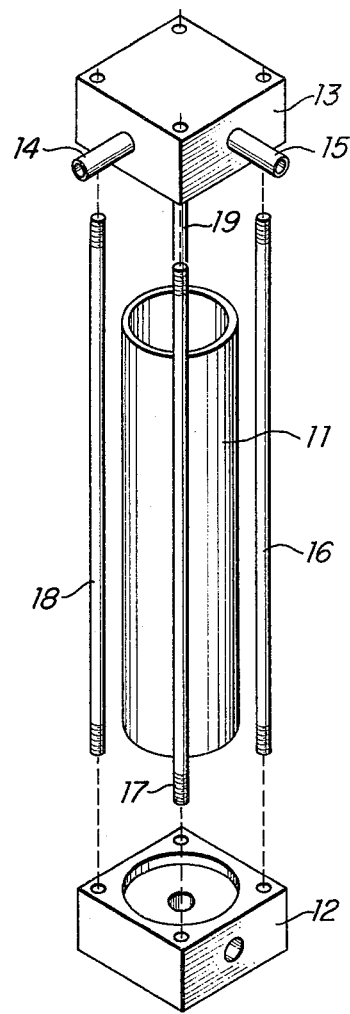
FIG. 2 is a perspective view illustrating the various components of a dispersion reservoir suitable for use in the cross flow filtration molding apparatus of FIG. 1.

The reservoir 10 is illustrated in FIG. 2. A cylindrical pressure vessel 11, designed to withstand elevated pressures, is mounted on base 12 which also serves as the drive for a magnetic stirrer (not shown) within pressure vessel 11. The stirrer serves, of course, to maintain a uniform dispersion of particles in vessel 11. Cover 13 is provided with two ports, 14 and 15. Port 14 is connected to a supply of compressed gas by pressure line 43 as shown in FIG. 1, so that pressure may be applied to dispersion in pressure vessel 11. Return port 15 connects to the dispersion return line 42, as illustrated in FIG. 1, so that dispersion which has passed through mold 30 can be recycled back to pressure vessel 11. As illustrated, reservoir 10 is assembled using four posts, 16, 17, 18 and 19, which have threaded ends allowing them to be screwed into base 12 and cover 13.

FIGS. 3 and 4 illustrate flow development module 20 in detail. Module 20 is optional, but has been found to improve the uniformity of the final product by minimizing end effects in mold 30, such as those created by an incompletely developed velocity profile.

Flow development module 20 consists of an elongated tube 21 having an inside diameter the same as that of mold 30. Jacket 22 can be used as a heat exchanger to remove heat generated during pumping by circulating a heat exchange medium in jacket 22. This is done by pumping the medium into jacket 22 through jacket inlet 23 and removing it through jacket outlet 24. Jacket 22 could alternately be used for cooling, or even refrigerating, dispersion prior to its entrance into mold 30.

Figure 6:
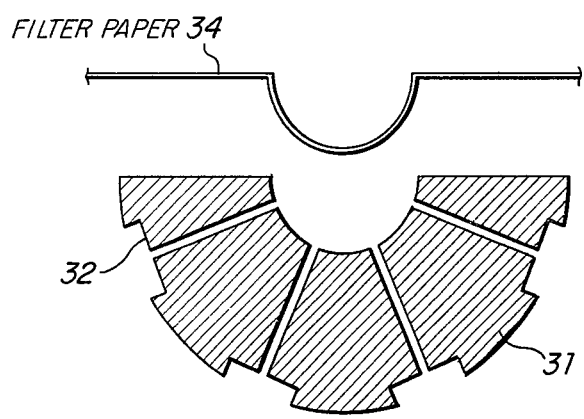

FIGS. 5 and 6 illustrate mold 30 in detail. As shown, mold 30 consists of a perforated tube 31 which is split lengthwise to facilitate easy removal of the shaped article. Tube 31 contains perforated sections 32 which allow transport of dispersion medium in the radial direction through the mold walls as dispersion is pumped through mold 30 in the longitudinal direction.

As illustrated in FIG. 6, it is often desirable to employ filter paper 34 in the mold. In these cases, filter paper 34 can be glued to each of the two halves of split tube 31 using a suitable adhesive such as a silicone or alkyl-alpha-cyanoacrylate adhesive.

Dispersion is pumped into tubular mold 30 at entrance 36 and passes from mold 30 at exit 38. As dispersion travels through mold 30, a fraction of its liquid medium is forced through filter paper 34 and subsequently through the pores in porous section 32 and thus through tube wall 31 where it evaporates into the atmosphere. Radial transport of the dispersion medium results in deposition of the particles onto the surface of filter paper 34. While transport of a fraction of medium and particles proceeds radially through tube wall 31, most of the dispersion is decanted since it flows through mold 30 in the axially direction to pump 40. Pump 40 then recirculates decanted polymer dispersion in return line 42 to reservoir section 10. Flow of dispersion through mold 30 is continued until sufficient wall thickness in the molded article has been achieved.

Mold 30 is designed specifically to produce hollow tubing using the cross flow filtration process described herein. It is clear, of course, that a wide variety of other mold shapes could also be employed. In fact, it is believed that the mold could be virtually any closed shape which has at least one port, although two ports are usually preferred. Thus, the mold might have the shape of an elbow, T-joint, bifurcated tubes, garment sleeves or even an entire T-shirt, or other shape.

Hydrostatic pressure applied to the dispersion is used to increase the rate of flow of medium through the porous walls of mold 30. This can conveniently be supplied by connecting a cylinder of compressed gas to reservoir port 14, but other methods can also be used. The amount of pressure necessary will vary with many factors, including the chemical composition, size, charge and concentration of particles; the chemical composition of the liquid medium; the shape, size, wall thickness, etc., of the article to be molded; and the size of pores in the mold walls. In the case of a dispersion of collagen or crosslinked collagen-mucopolysaccharide particles, for example, the pressure applied should be at least about five p.s.i.g. to achieve a practical rate of medium transport through the mold walls. With larger particles, lower pressures can be used. Also, the desired pressure difference across the mold wall can be established by applying vacuum to the mold exterior.

The wall thickness of the tube produced in mold 30 can be varied. This is primarily done by adjusting the molding time, but other factors such as the dispersion flow rate, the hydrostatic pressure applied, the dispersion concentration, etc. also affect wall thickness.

After the formation of the shaped article, it is often desirable to emloy a post treatment to increase its structural integrity. Many different types of post treatment are suitable, including: introduction of chemical bonds, such as by crosslinking; heat sealing of material, such as polyester or polyamide fibers, by controlled application of heat; solvent sealing; sintering of particles, such as coalesce of rubber latex particles by drying of suspending liquid medium; or other treatments.

It is advantageous to remove entrained air bubbles from the dispersion prior to processing in the apparatus described herein. This can be done by centrifuging the dispersion at a low speed or by the use of antifoam substances or other methods. Removal of air bubbles improves the stability of the dispersion during storage and processing. In addition, removal of bubbles leads to fabrication of articles with smooth interior surfaces.

The apparatus and method described herein are particularly useful for forming shaped articles from dispersions of particles which are often very difficult or impossible to form by other methods. An example of such materials is a dispersion of the crosslinked collagen-mucopolysacchride products described above in an aqueous medium. Seamless, hollow articles, such as seamless straight or bifurcated tubes, and other complicated shapes can be formed from these biocompatible materials using the apparatus and process of this invention.

Although the specific description herein is mostly in terms of using the apparatus and process described for molding particles from crosslinked collagen-mucopolysaccharide polymers, many other particles can be employed. The apparatus and method offer distinct advantages, for example, in forming objects from insoluble and/or infusible particles. Of course, articles could also be formed from materials, such as thermoplastic polyester particles or fibers, which can be molded using more traditional processes. For example, a suspension of chopped polyester strands or of polyamide fibers could be used to form a desired three-dimensional mat or nonwoven fabric, such as the sleeve of a garment, by using cross flow filtration molding to deposit the fibers on the inside wall of a mold cavity.

Some examples of dispersions of particles other than those of crosslinked collagen-mucopolysaccharide products which could be utilized include, but are not limited to, paper pulp, starch dispersions, soya bean protein dispersions, collagen fiber dispersions, cotton fiber and chemically modified cotton fiber dispersions, wool fibers, glass fiber dispersions, polyester and nylon fiber dispersions and other dispersions of solid or solid-like particles of organic polymers or of ceramic materials. Another example is the deposition of latex particles on the mold, to form a very concentrated solid-like material which could then be air dried to cause sintering or coalescence of latex particles.

The method and apparatus described herein can now be illustrated more specifically by way of specific examples.

EXAMPLE 1

The raw material for molding was a bovine hide collagen/chondroitin 6-sulfate dispersion prepared as follows: Three grams of bovine hide collagen in particulate form was dissolved in 400 grams of 0.05 M acetic acid, pH 3.5. The solution was maintained at 4° C. A chondroitin 6-sulfate solution prepared by dissolving 0.3 grams chondroitin 6-sulfate in 40 grams water, was added to precipitate a collagen-chondroitin 6-sulfate particle suspension, and additional acetic acid was added to adjust the pH to about 2.9.

The total amount of collagen-chondroitin 6-sulfate dispersion used was first treated in a homogenizer and then fed into an air-pressurized Plexiglas tank similar to the pressure vessel illustrated in FIG. 1. A magnetic stirrer bar served to minimize particle concentration gradients inside the vessel. Dispersion exited from the bottom of the pressure vessel and flowed into a flow development module and perforated aluminum tube split lengthwise which acted as a mold for tubes. Filter paper was carefully glued to each of the two halves of the aluminum tubes using alpha cyanoacrylate adhesive. The flow development module and mold had an inside diameter of 0.25 inches and the flow development module was 17 in. long whereas the mold was 10.5 in. long. Additionally, the perforated aluminum tubing had a series of 0.03" pores extending linearly every 45° of circumference and positioned every 0.01".

Upon entry into the tubular mold, a fraction of the water of the dispersion was forced through the filter paper and subsequently through the perforations in the tube wall where it evaporated into the atmosphere giving the outside of the mold a "sweating" appearance. Radial transport of the dispersion water was accompanied by transport and deposition of collagen/chondroitin 6-sulfate particles onto the filter paper surface.

While transport of a fraction of water and particles proceeded radially inside the tube mold, the decanted bulk of the dispersion inside the mold flowed uneventfully in the axial direction and was pumped back to the pressure vessel through a dispersion return line where it was stirred and recycled back into the mold.

At an applied pressure of 30 psig, and a flow rate of approximately 2.5 ml/min, a gel layer of about 0.004 inches thick had formed after a period of about 6 hours of operation which, when air dried after decanting the non-gelled fluid, was sufficiently concentrated to be handled without loss of shape. Tubes fabricated in this manner were removed from the tubular mold without being detached from the filter paper and were subjected to an insolubilization (crosslinking) treatment by immersion in 250 ml of 0.5% w/w glutaraldehyde solution for 24 hours. The 10-inch tube obtained has a thickness of 0.0028, 0.0030, 0.0034, 0.0034 and 0.0034 inches at distances of 2, 4, 6, 8 and 10 inches, respectively, from the upstream end of the tube.

EXAMPLE 2

The procedure and apparatus of Example 1 were used except as follows.

The raw material was a bovine hide collagen dispersion, concentration 3 grams air-dry collagen per 400 grams of a 0.05 M acetic acid solution. At an applied pressure of 35 p.s.i.g., a flow rate of 3.1 g/min was observed in the flow development module corresponding to a velocity of 9.7 cm/min. After about 3.5 hours of filtration, the mold was opened, the filter paper removed and the formed collagen tube was crosslinked by immersion in 250 ml of 0.5% w/w aqueous glutaraldehyde solution for 24 hours and was then dried. The wall thickness of the dry tube was measured at various points along its length and found to be 0.0015, 0.0016, 0.0016, 0.0016 and 0.0010 in. at 2, 4, 6, 8 and 10 in., respectively, along its length.

EXAMPLE 3

The apparatus and procedure of Example 1 were used. The dispersion was a collagen dispersion. The collagen used was bovine hide collagen that was obtained from the Department of Agriculture as a dried matted material. The collagen was shredded to a line particle size and then 1% by weight was dispersed in 0.5 M acetic acid, pH 3.5, in a Waring Blender. The collagen was not completely native, containing up to 30% gelatin.

The results for six runs are presented in the following table.

| Run # | Solution Conc. | Pressure psi | Duration Of Run hr | Flow Rate ml/min | Total Flux Volume ml | Dry Tube Thickness (mils) | | | | |
|---|---|---|---|---|---|---|---|---|---|---|
| | | | | | | 2"[a] | 4" | 6" | 8" | 10" |
| 1 | 3 gr/400 ml | 35 | 3½ | — | — | — | — | — | — | — |
| 2 | 3 gr/400 ml | 35 | 2⅔ | 7.5 | — | 1.7 | — | 2.1 | 1.8 | 2.0 |
| 3 | 3 gr/400 ml | 35 | 1 | — | — | .3 | — | .5 | .6 | .7 |
| 4 | 3 gr/500 ml | 35 | 3⅔ | 7.5 | 100 | 1.1 | 1.0 | 1.2 | 1.7 | 1.2 |
| 5 | 1 gr/400 ml | 35 | 2½ | 4 | 100 | 1.5 | 1.9 | 1.6 | 1.2 | 1.3 |
| 6 | 3 gr/400 ml | 35 | 4 | 8 | 85 | 1.5 | 1.6 | 1.6 | 1.6 | 1.0 |

[a]Inches along length, starting at upstream end

EXAMPLE 4

The apparatus and procedure of Example 1 were used.

The dispersion was a collagen-mucopolysaccharide prepared from the collagen dispersion of Example 3. To produce the collagen/chondroitin 6-sulfate composite, 10% by weight chondroitin 6-sulfate was dissolved in distilled water and slowly added by burette to the stirred collagen dispersion dropwise. The chondroitin 6-sulfate solution precipitated the collagen to form a stringy fibrous complex. The solution was then redispersed in the Waring Blender to form a collagen-mucopolysaccharide dispersion at pH 3.7. Under continued blending, additional acetic acid was added dropwise to the collagen-mucopolysaccharide, pH 3.7, solution until the pH was lowered to PH 2.9. This served to help return the collagen-mucopolysaccharide composite to a dissolved, viscous, gel-like fluid. The entire process was performed at a low enough temperature to ensure that no additional denaturation of the collagen occurred. Thus, refrigerated acetic acid and a refrigerated blender were employed.

The results for eight runs are presented in the following table.

| Run # | Pressure psi | Duration Of Run hr | Flow Rate ml/min | Total Volume Flux ml | Thickness Measurements (mils) | | | | |
|---|---|---|---|---|---|---|---|---|---|
| | | | | | 2"[a] | 4" | 6" | 8" | 10" |
| 1 | 30 | ½ | — | — | 1.3 | 1.5 | 1.5 | 1.6 | 1.8 |
| 2 | 30 | 4 | 5 | 75 | 3.2 | 4.0 | 3.95 | 3.85 | 4.15 |
| 3 | 20 | 2 | 4 | 40 | 2.95 | 3.3 | 3.7 | 3.5 | 3.8 |
| 4 | 30 | 2 | 2.5 | 55 | 2.8 | 3.05 | 3.35 | 3.4 | 3.35 |
| 5 | 30 | 2 | 10 | 110 | 2.65 | 3.3 | 3.3 | 3.45 | 3.5 |

-continued

| Run # | Pressure psi | Duration Of Run hr | Flow Rate ml/min | Total Volume Flux ml | Thickness Measurements (mils) | | | | |
|---|---|---|---|---|---|---|---|---|---|
| | | | | | 2"a | 4" | 6" | 8" | 10" |
| 6 | 35 | 2 | 4 | 115 | 2.5 | 3.0 | 3.2 | 4.3 | 4.25 |
| 7 | 30 | 6 | 2.5 | 140 | 3.4 | 3.35 | 3.45 | 4.2 | 3.5 |
| 8 | 10 | 2 | 8 | 100 | 1.3 | 2.9 | 3.8 | 5.4 | 4.0 | aInches along length, starting at upstream end

EXAMPLE 5

The apparatus and procedure of Example 1 were used, except that the molding pressure was varied and molding time was two hours. The dispersion was that described in Example 4. The results of four runs are presented in the following table.

| Molding Pressure psi | Dry Thickness (mils) | | | | | |
|---|---|---|---|---|---|---|
| | 2"a | 4" | 6" | 8" | 10" | Average |
| 10 | 1.3 | 2.9 | 3.8 | 5.4 | 4.0 | 3.5 |
| 20 | 3.0 | 3.3 | 3.7 | 3.5 | 3.8 | 3.5 |
| 30 | 2.8 | 3.0 | 3.4 | 3.4 | 3.4 | 3.2 |
| | 2.6 | 3.3 | 3.3 | 3.4 | 3.5 | 3.2 |
| 35 | 2.5 | 3.0 | 3.2 | 4.3 | 4.2 | 3.4 | aInches along length, starting at upstream end

Those skilled in the art will recognize many equivalents to the specific embodiments of the apparatus or specific steps of the process described herein. The following claims are intended to cover such eqivalents.

What is claimed is:

1. A cross flow filtration process for molding articles in a predetermined shape from dispersions of particles in a liquid medium, comprising:
   a. pumping said dispersion in a continuous flow from an input port to an output port through a mold, the interior walls of which are formed in said predetermined shape, said walls being porous to allow transport of a portion of said dispersion through the pores in said walls under a pressure differential thereby causing particles in said dispersion to deposit on said mold walls and the liquid medium to pass to the outside of the mold;
   b. applying a pressure differential across the porous walls of said mold to drive such portion of said dispersion through the porous walls as dispersion is pumped through said mold between said input and output ports;
   c. collecting the remaining portion of said dispersion at the output port; and
   d. maintaining said flow until said deposit has accumulated on said walls to predetermined thickness.

2. The process of claim 1 in which the walls form a generally cylindrical body and the flow between input and output ports is generally axially directed.

3. The process of claim 2 in which the dispersion is filtered before passing through the pores in said walls.

4. A method of claim 1 wherein said particles are comprised of a polymer.

5. A method of claim 1 wherein said polymeric particles are a collagen-mucopolysaccharide reaction product.

* * * * *